US009380698B1

(12) United States Patent
Li et al.

(10) Patent No.: US 9,380,698 B1
(45) Date of Patent: Jun. 28, 2016

(54) STRETCHABLE ELECTRONIC PATCH HAVING A FOLDABLE CIRCUIT LAYER

(71) Applicant: VivaLnk Limited (Cayman Islands), Santa Clara, CA (US)

(72) Inventors: Jiang Li, Cupertino, CA (US); Junfeng Mei, Sunnyvale, CA (US)

(73) Assignee: VivaLnk, Inc., Santa Clara, CA (US)

(*) Notice: Subject to any disclaimer, the term of this patent is extended or adjusted under 35 U.S.C. 154(b) by 0 days.

(21) Appl. No.: 14/644,183

(22) Filed: Mar. 10, 2015

Related U.S. Application Data

(63) Continuation-in-part of application No. 14/616,986, filed on Feb. 9, 2015.

(60) Provisional application No. 62/088,399, filed on Dec. 5, 2014.

(51) Int. Cl.

| | |
|---|---|
| *G06K 7/08* | (2006.01) |
| *G06K 19/02* | (2006.01) |
| *G06K 19/06* | (2006.01) |
| *H05K 1/02* | (2006.01) |
| *H05K 1/03* | (2006.01) |
| *H05K 1/18* | (2006.01) |
| *H05K 1/14* | (2006.01) |
| *A61B 5/00* | (2006.01) |
| *H04B 1/3827* | (2015.01) |
| *H04B 5/00* | (2006.01) |

(52) U.S. Cl.
CPC ............ *H05K 1/0283* (2013.01); *A61B 5/6833* (2013.01); *H04B 1/385* (2013.01); *H04B 5/0056* (2013.01); *H05K 1/0393* (2013.01); *H05K 1/14* (2013.01); *H05K 1/189* (2013.01); *H04B 2001/3866* (2013.01); *H05K 2201/09027* (2013.01)

(58) Field of Classification Search
USPC .................. 235/451, 492, 375, 488
See application file for complete search history.

(56) References Cited

U.S. PATENT DOCUMENTS

| | | | | |
|---|---|---|---|---|
| 4,694,283 | A * | 9/1987 | Reeb ............... | G08B 13/2417 257/E27.114 |
| 5,529,502 | A * | 6/1996 | Peltier ............... | H01R 12/774 439/493 |
| 5,749,365 | A * | 5/1998 | Magill ............... | A61B 5/0008 128/903 |
| 2005/0146510 | A1* | 7/2005 | Ostergard ........... | G06F 3/044 345/173 |
| 2007/0270672 | A1 | 11/2007 | Hayter | |
| 2008/0068175 | A1* | 3/2008 | Hockey ............. | G06K 19/0726 340/572.7 |
| 2008/0156886 | A1* | 7/2008 | Tsuchiya ........... | G06K 19/07749 235/492 |
| 2008/0186241 | A1* | 8/2008 | Christensen ......... | A61B 5/0028 343/718 |
| 2009/0171180 | A1 | 7/2009 | Pering | |
| 2012/0242481 | A1 | 9/2012 | Gernandt | |
| 2013/0258575 | A1* | 10/2013 | Rothkopf ........... | G06F 1/1626 361/679.31 |
| 2014/0061584 | A1* | 3/2014 | Mahan .............. | H01L 23/4334 257/13 |
| 2015/0156879 | A1* | 6/2015 | Pouget ............... | H05K 1/148 361/749 |

* cited by examiner

*Primary Examiner* — Tuyen K Vo
(74) *Attorney, Agent, or Firm* — SV Patent Service

(57) ABSTRACT

An electronic patch includes a foldable circuit layer that includes a foldable network that includes comprising: a plurality of electronic modules comprising a plurality of electronic components, and flexible straps that connect the plurality of electronic modules, wherein the flexible straps comprise conductive circuit that are conductively connected with the plurality of electronic components in the plurality of electronic modules. Neighboring electronic modules can undulate in opposite directions normal to the foldable circuit layer. The electronic patch also includes an elastic layer that encloses the foldable circuit layer.

17 Claims, 13 Drawing Sheets

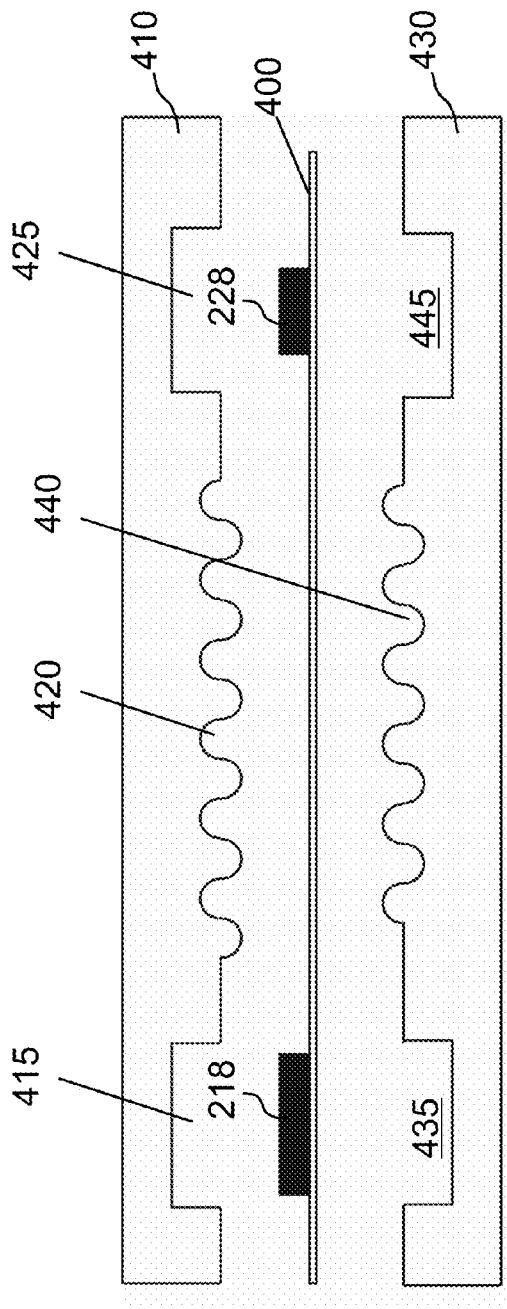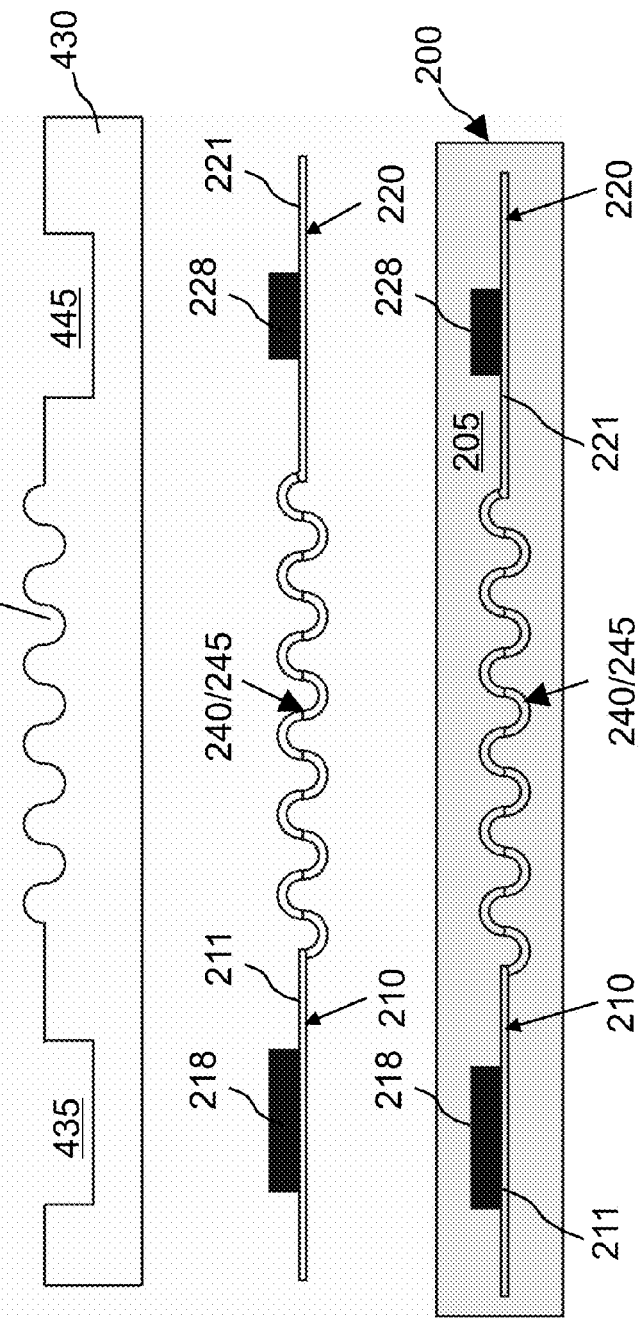

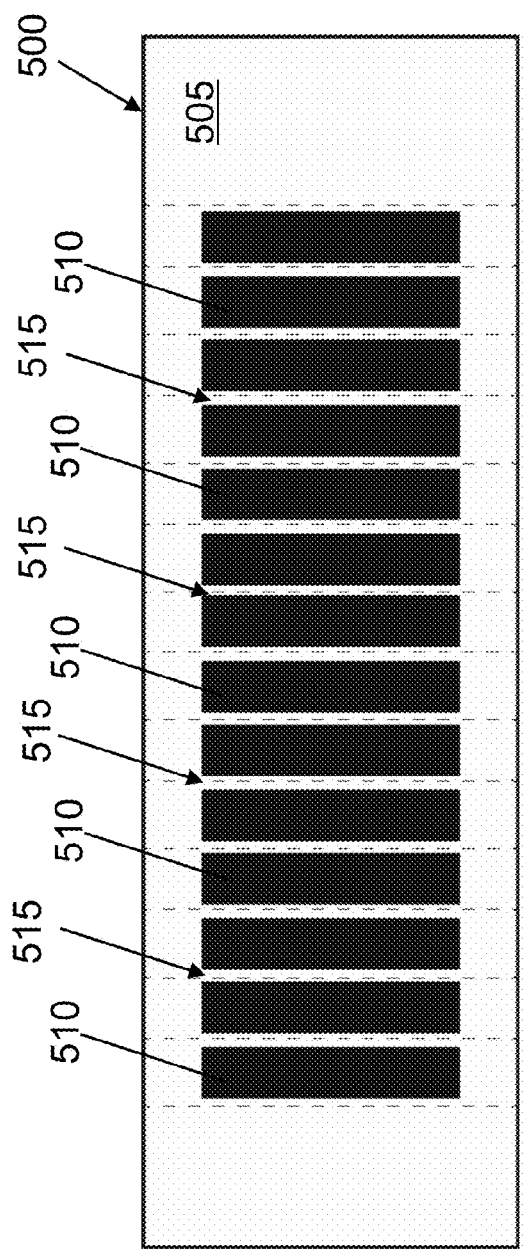
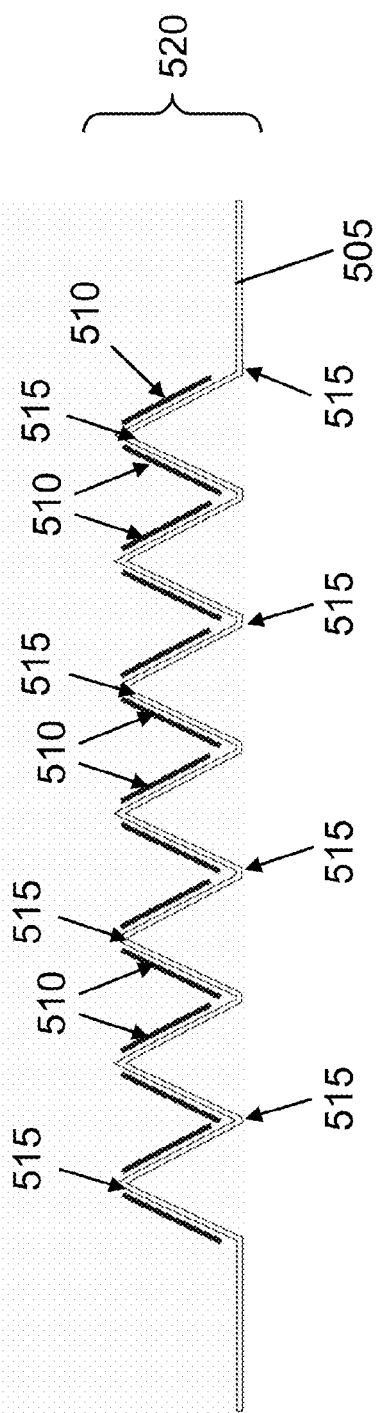
Fig. 5A
Fig. 5B

STRETCHABLE ELECTRONIC PATCH HAVING A FOLDABLE CIRCUIT LAYER

BACKGROUND OF THE INVENTION

The present application relates to electronic devices, and in particular, to electronic patches that can adhere to human skin or the surface of an object, including curved surfaces.

Wearable tags are a specific type of electronic patches. In general, electronic patches or stickers can be attached not only to human bodies but also to other objects such as merchandized goods such as computers, machineries, and clothes, packaging material and shipping boxes. Electronic patches can communicate with smart phones or other devices wirelessly, through NFC, Bluetooth, WiFi, or other methods.

Electronic patches can be used for tracking objects, for performing functions such as producing sound, light or vibrations, and so on. As the applications and human needs become more sophisticated and complex, there are a rapidly increasing number of tasks that electronic patches are required to perform. Because of the complex curvatures of the objects, the electronic patches are often required to be conformal to curved surfaces. In addition, the curvature of an object may vary overtime.

Wearable tags or patches can communicate with smart phones and other devices using WiFi, Bluetooth, or NFC technologies. Near Field Communication (NFC) is a wireless communication standard which enables two devices in a short range to establish a communication channel within a short period of time through radio waves in the 13.56 MHz frequency range. NFC can be a useful technology for data transfer between two devices in close proximity to one another. Because it needs the two devices to be in close proximity to one another (less than 10 cm), it is more secure than other wireless technologies like Bluetooth and Wi-Fi. Hence, it can be seen as an easy and secure tool for establishing quick two-way connections for data transfer. NFC is a two-way communication tool, one of the devices/cards can have a passive NFC tag that can reduce the cost and still behave in the same way as any other RFID tag.

Bluetooth is another wireless technology standard for exchanging data over relatively long distance in tens of meters. It uses short wavelength UHF radio waves from 2.4 to 2.485 GHz from fixed or mobile devices. Bluetooth devices have evolved to meet the increasing demand for low-power solutions that is required for wearable electronics. Benefited from relatively longer reading distance and active communication, Bluetooth module help wearable patches to continuously monitoring vital information without any human interference, which gives Bluetooth advantage over NFC solution in many applications.

Wearable tag (or patch) is an electronic patch that can be worn by a user. A wearable electronic patch is required to directly stay on user's skin and function for an extended period of time from hours to months. An electronic patch can contain a micro-electronic system and can be accessed using NFC, Bluetooth, WiFi, or other wireless technologies. An authentication wearable tag can be used as a "password" similar to a barcode. For example, it can be used to recognize a user's smart phone for authentication purpose. It can also be integrated with different sensors for other purposes such as vital signs monitoring, motion track, skin temperature measurements and ECG detection.

Despite initial development efforts, conventional wearable devices still face several drawbacks: they may not provide adequate comfort for users to wear them; they may not stay attached to user's body for the required length of time; they are usually not aesthetically appealing.

A wearable electronic patch that has sensor, computation, and communication functions usually require multiple semiconductor chips assembled on flexible printed circuits. Semiconductor chips are rigid and have three dimensions while printed circuits are made of polymer substrate that can be flexible but not deformable to respond to curvature change of the skin commonly due to muscle movements underneath. Human skin can move around with high percentage of deformation, whereas a conventional electronic patch cannot move with the same amount of strains as the skin, which is one reason for user's feeling of discomfort.

Another drawback of conventional electronic patches is that the rigid polymer substrate does not allow much breathability to the skin. The build-up of sweat and moisture can cause discomfort and irritation to the skin, especially after wearing it for an extended period of time. In addition, their rigid substrates are very difficult to conform to curved surfaces.

Moreover, conventional wearable devices are often not robust enough to sustain repeated elongations during the movements of the body that the electronic patches are attached to. Under stress, different layers in electronic patches can break or delaminate rendering the patches inoperable.

There is therefore a need for more flexible electronic patches that can stick to skin longer and are also comfortable for users to wear.

SUMMARY OF THE INVENTION

The presently disclosure attempts to address the aforementioned limitations in conventional electronic patches. The disclosed electronic patches are highly compliant and more stretchable, while also being able to support the circuit, chips, and other electronic components in the wearable electronic patches. The disclosed electronic patches can change their physical shape and dimension to relieve stresses such as repeated elongations, therefore increasing durability. The disclosed electronic patches can stay attached to skin for longer period of time enduring muscle movements while providing constant contact to the skin.

The disclosed electronic patches are also breathable. The stretchability and the breathability make the disclosed electronic patches more comfortable for the users.

In one general aspect, the present invention relates to an electronic patch includes a foldable circuit layer that includes a foldable network that includes comprising: a plurality of electronic modules comprising a plurality of electronic components, and flexible straps that connect the plurality of electronic modules, wherein the flexible straps comprise conductive circuit that are conductively connected with the plurality of electronic components in the plurality of electronic modules. Neighboring electronic modules can undulate in opposite directions normal to the foldable circuit layer. The electronic patch also includes an elastic layer that encloses the foldable circuit layer.

Implementations of the system may include one or more of the following. The plurality of electronic modules can include a first electronic module; second electronic modules on two sides of the first electronic module along a first planar direction; third electronic modules on two sides of the first electronic module along a second planar direction, wherein the first electronic module can undulate in a direction opposite to undulation directions of the second electronic modules and the third electronic modules. The first electronic module and the second electronic modules can be positioned in a row, wherein the first electronic module and the third electronic modules can be positioned in a column perpendicular to the row. The plurality of electronic modules and the flexible straps can define holes therein, which in part forms the foldable network. The elastic layer can have a Young's Modulus lower than 0.3 Gpa. The elastic layer can include an elastomeric material or a viscoelastic polymeric material. The plurality of electronic modules can be formed on support substrates. The support substrate can have a Young's Modulus higher than 0.5 Gpa. The first support substrate can have Polyimide, Polyethylene, Terephthalate, PEEK, Polyester, Aramid, Composite, Glass epoxy, and Polyethylene naphalate. The electronic components in the plurality of electronic modules can have one or more semiconductor chips. The one or more semiconductor chips can wirelessly communicate with an external device. The electronic components in the plurality of electronic modules can include an antenna circuit configured to receive or transmit wireless signals in communications with the external device. The one or more semiconductor chips in combination with the first conductive circuit or the second conductive circuit can wirelessly communicate with the external device based on near field communication (NFC), Wi-Fi, Bluetooth, or RFID wireless communication standard. The electronic components in the plurality of electronic modules can include capacitors, inductors, resistors, metal pads, diodes, transistors, or amplifiers.

In another general aspect, the present invention relates to an electronic patch that includes a foldable circuit layer comprising: a foldable substrate comprising a plurality of sections separated by fold lines, wherein the foldable substrate is configured to be folded along the fold lines; a conductive circuit; and a plurality of electronic components on different sections in the plurality of sections, wherein the conductive circuit is configured to connect the plurality of electronic components across the plurality of sections; and an elastic layer that encloses the undulated circuit layer.

Implementations of the system may include one or more of the following. The substrate cross-sectionally can have a zig-zag shape. The fold lines can be substantially parallel to each other.

In another general aspect, the present invention relates to an electronic patch, comprising: a first circuit layer comprising a substantially flat first substrate and a first conductive circuit; a second circuit layer comprising a substantially flat second substrate and a second conductive circuit; an undulated ribbon that connects the first circuit layer and the second circuit layer, wherein the undulated ribbon includes a third conductive circuit that connects the first conductive circuit and the second conductive circuit; and an elastic layer that encloses the first circuit layer, the second circuit layer, and the undulated ribbons.

Implementations of the system may include one or more of the following. The undulated ribbon can be undulated in a direction normal to the substantially flat first substrate or the substantially flat second substrate. The undulated ribbon can have serpentine or zigzag shape that includes turns, folds, or loops out of a plane of the substantially flat first substrate or the substantially flat second substrate. The substantially flat first substrate and the substantially flat second substrate can be substantially parallel to each other. The undulated ribbon can be fabricated by pressing a flat circuit layer by molds comprising recesses having undulated contours. The electronic patch can further include: multiple undulated ribbons that connect the first circuit layer and the second circuit layer, wherein the multiple undulated ribbons define at least one opening therein. The first support substrate can have a Young's Modulus higher than 0.5 Gpa. The first support substrate can include Polyimide, Polyethylene, Terephthalate, PEEK, Polyester, Aramid, Composite, Glass epoxy, and Polyethylene naphalate. The undulated ribbon can have a Young's Modulus lower than 0.3 Gpa. The elastic layer can have a Young's Modulus lower than 0.3 Gpa. The elastic layer can include an elastomeric material or a viscoelastic polymeric material. At least one of the first circuit layer or the second circuit layer can include one or more semiconductor chips in connection with the first conductive circuit and the second conductive circuit. The one or more semiconductor chips in combination with the first conductive circuit or the second conductive circuit can wirelessly communicate with an external device. At least one of the first conductive circuit or the second conductive circuit can include an antenna circuit that can receive or transmit wireless signals in communications with the external device. The one or more semiconductor chips in combination with the first conductive circuit or the second conductive circuit can wirelessly communicate with the external device based on near field communication (NFC), Wi-Fi, Bluetooth, or RFID wireless communication standard. The electronic patch can further include an adhesive layer under the elastic layer and configured to adhere to a user's skin. At least one of the first circuit layer or the second circuit layer can include one or more sensors, actuators, or chemical delivery devices in connection with the conductive circuit. At least one of the first circuit layer or the second circuit layer can include one or more electronic components selected from the group consisting of capacitors, inductors, resistors, metal pads, diodes, transistors, and amplifiers.

These and other aspects, their implementations and other features are described in detail in the drawings, the description and the claims.

BRIEF DESCRIPTION OF THE DRAWINGS

FIGS. 4A-4C are cross-sectional views showing the fabrication of an exemplified stretchable wearable electronic patch in accordance with some embodiments of the present invention.

FIGS. 5A-5C are respectively top and cross-sectional views of an exemplified stretchable wearable electronic patch having foldable circuit layer in accordance with some embodiments of the present invention.

DETAILED DESCRIPTION OF THE INVENTION

Figure 1:
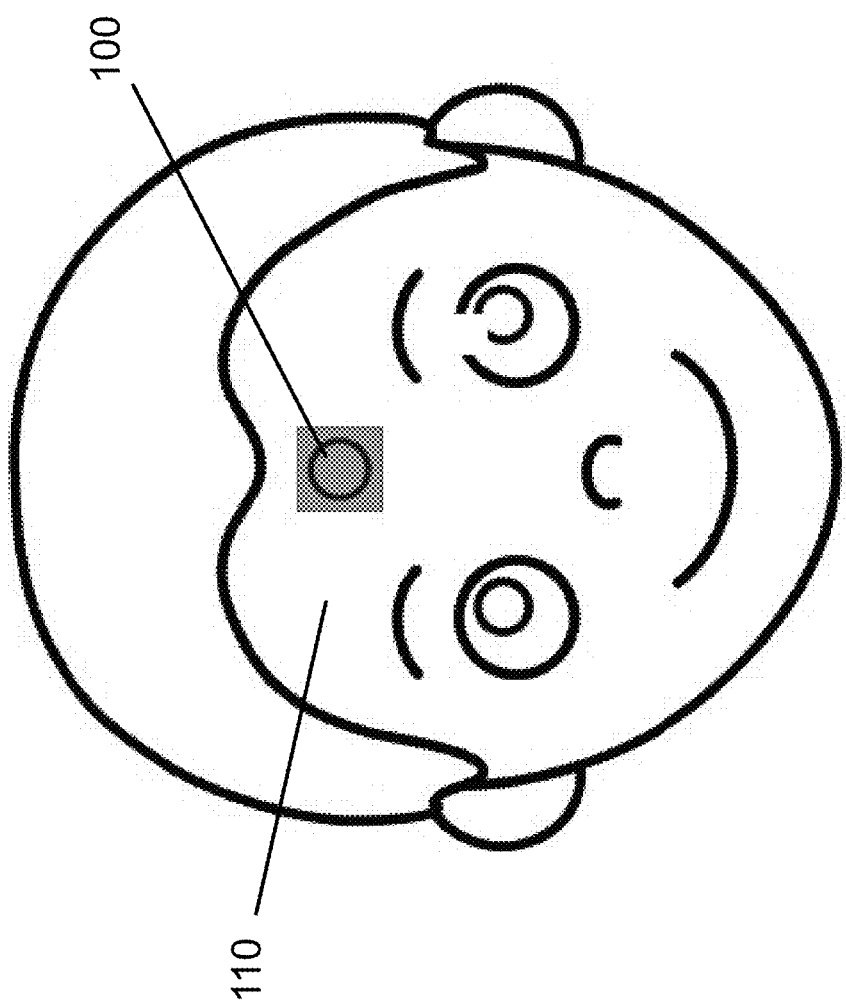
FIG. 1 illustrates the usage of a wearable electronic patch that is attached to a user's skin.

Referring to FIG. 1, an electronic patch 100 adheres to a person's skin 110 for measuring body vital signs. The electronic patch 100 can be placed on forehead, hand, wrist, arm, shoulder, waist, leg, foot, or other parts of the body. In the present application, the term "electronic patch" can also be referred to as "electronic sticker" or "electronic tag".

As discussed above, wearable electronic patches face several challenges: people's daily activities such as taking showers or bathes, swimming, exercises, holding weights, etc. involve muscle and skin movements. The electronic patches thus need to responsively change their physical dimensions to be able to adhere to the skin for extended periods of time. The electronic patches may also be rubbed by clothing, hands, or other objects numerous times a day. While Band-Aid patches usually cannot on skin for more than a week, conventional electronic patches normally have much stiffer substrates, which makes them more easily rubbed off than Band-Aid stickers. In addition, conventional electronic patches are not comfortable to wear because they are not stretchable, inflexible, and not breathable.

Figure 2A:
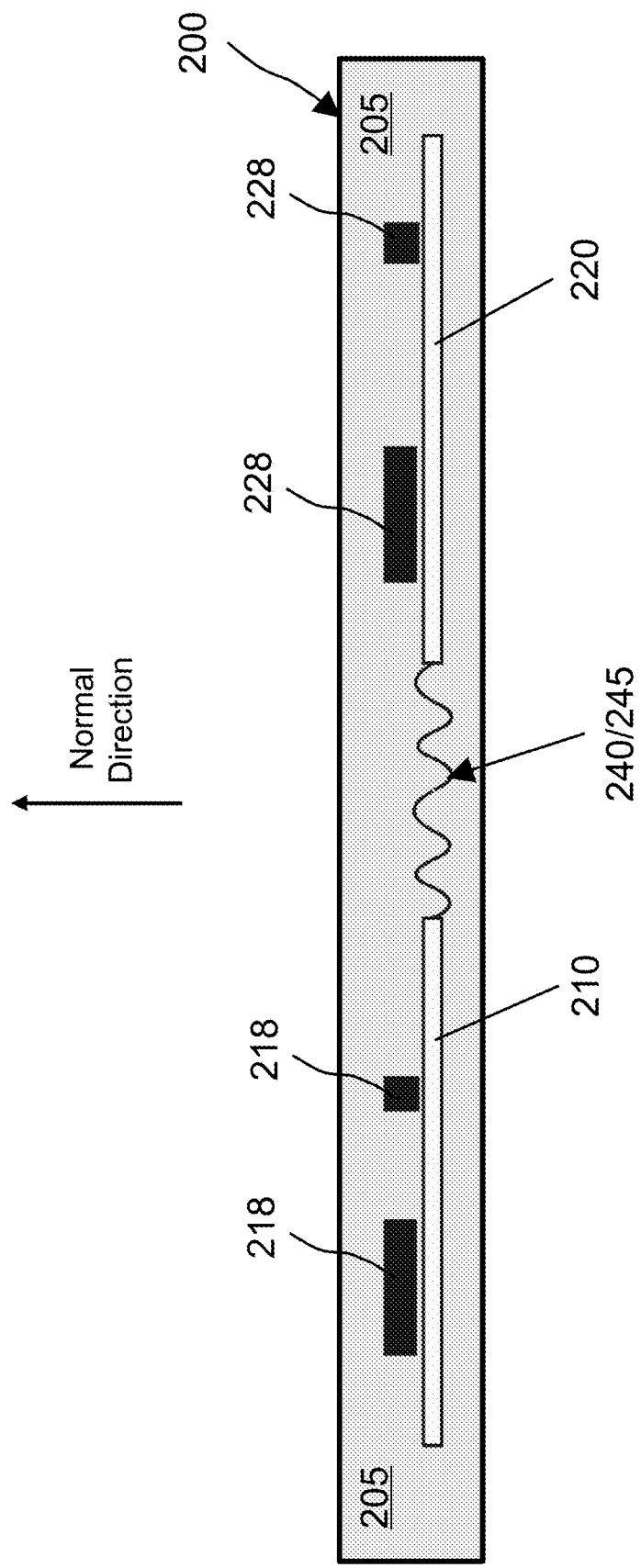
FIGS. 2A and 2B are respectively a cross-sectional and a perspective view of an exemplified stretchable wearable electronic patch in accordance with some embodiments of the present invention.
Figure 2B:
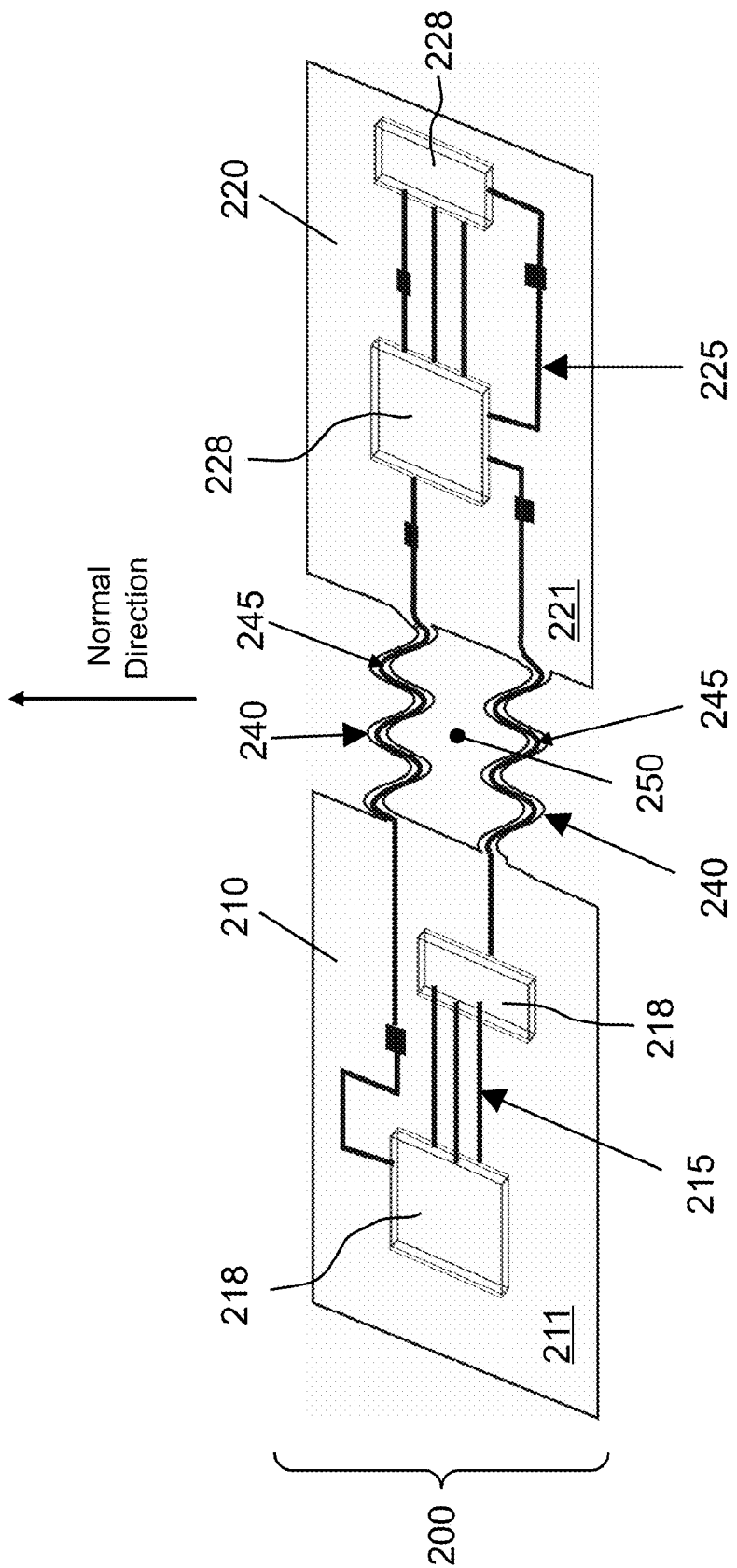

The presently disclosure aims to overcome the drawbacks in the conventional electronic patches, and to provide highly stretchable, compliant, and durable wearable wireless patches that are also comfortable for users to wear. Referring to FIGS. 2A and 2B, an electronic patch 200 includes an elastic layer 205, a first circuit layer 210, a second circuit layer 220, and one or more undulated ribbons 240 that connect the first circuit layer 210 and the second circuit layer 220. The widths of the one or more undulated ribbons 240 are much larger than their thicknesses. The first circuit layer 210 and the second circuit layer 220 are substantially flat and are substantially parallel to each other. The first circuit layer 210, the second circuit layer 220, and the one or more undulated ribbons 240 are embedded or enclosed in the elastic layer 205.

The first circuit layer 210 includes a conductive circuit 215 and one or more semiconductor chips 218. The second circuit layer 220 includes a conductive circuit 225 and one or more semiconductor chips 228. The one or more undulated ribbons 240 include a conductive circuit 245 that connects the conductive circuit 215 and the conductive circuit 225 respectively in the first circuit layer 210 and the second circuit layer 220. The conductive circuit 245 can be laid on or embedded in one of the undulated ribbons 240.

The conductive circuit 215 and the conductive circuit 225 can optionally include an antenna circuit, which by working with the semiconductor chips 218, 228 can communicate with external devices based on NFC standard, RFID, Wi-Fi, Bluetooth, or other types of wireless communication standard. Examples of external devices include smart phones, computers, mobile payment devices, scanners and readers (e.g. RFID readers), medical devices, security systems, personal identification systems, etc. Wireless communications compatible with the electronic patch 200 include NFC in a frequency range near 13.56 MHz, UHF RFID at about 915 MHz, Bluetooth in 2.4 GHz or 5 GHz frequency ranges, and so on.

The first circuit layer 210 and the second circuit layer 220 can include electronic components such as the semiconductor chips, resistors, capacitors, inductors, diodes (including for example photo sensitive and light emitting types), sensors, transistors, amplifiers. The sensors can also measure temperature, acceleration and movements, and chemical or biological substances. The electronic components can also include electromechanical actuators, chemical injectors, etc. The semiconductor chips 218, 228 can perform communications, logic, signal or data processing, control, calibration, status report, diagnostics, and other functions.

The elastic layer 205 is made of a non-conductive material such as an elastomeric material or a viscoelastic polymeric material. The elastic layer 205 serves as a polymer matrix for the first circuit layer 210, the second circuit layer 220, and the one or more undulated ribbons 240. The elastic layer 205 can be made of a material having low Young's modulus and high failure strain. In some embodiments, the elastic layer 205 has Young's Modulus <0.3 Gpa. In some cases, the elastic layer 205 and can have Young's Modulus <0.1 Gpa to provide enhanced flexibility and tackability. Materials suitable for the elastic layer 205 include elastomers, viscoelastic polymers, such as silicone, and medical grade polyurethane that is a transparent medical dressing used to cover and protect wounds with breathability and conformation to skin.

The first circuit layer 210 and the second circuit layer 220, on the other hand, include support substrates 211, 221 that are made of sufficiently rigid materials to support to the conductive circuits 215, 225 and the semiconductor chips 218, 228. In some embodiments, the first circuit layer 210 and the second circuit layer 220 can have Young's Modulus larger than 0.5 Gpa, such as in a range between 1.0-10 Gpa. Examples of materials suitable for the first circuit layer 210 and the second circuit layer 220 include Polyimide, polyester, Aramid, Composite, Glass epoxy, and Polyethylene naphalate. In some embodiments, the first circuit layer 210 and the second circuit layer 220 are thicker than 0.001 mm to allow enough strength to support the circuits and chips during manufacturing process. The first circuit layer 210 and/or the second circuit layer 220 can include one or more layers of conductive metals to provide additional wiring capabilities. In some embodiments, the first circuit layer 210 and the second circuit layer 220 are thinner than 0.2 mm to provide flexibility and bendability to the electronic patch 200.

The one or more undulated ribbons 240 have curved or wavy shapes that undulate in the normal direction perpendicular to the planar directions of the electronic patch 200. The one or more undulated ribbons 240 can also be characterized having serpentine or zigzag shapes that have turns, folds, or loops out of the plane of the electronic patch 200 or the first circuit layer 210 and the second circuit layer 220.

When the electronic patch 200 is worn on a user's skin, the user skin often stretches (or compresses) in response to user's body (thus muscle) movements, thus conforming to user's skin in different moving positions. In response, the undulated ribbons 240 can elongate by unfolding at least partially some of their curved or wavy shapes without exerting excessive tensions on the conductive circuits 215, 225, 245, or on the semiconductor chips 218, 228. Thus the conductive circuits 215, 225, 245 and electronic components can stay intact and maintain normal functions under repeated stretches and compressions when the electronic patch 200 is worn on a user's skin.

Moreover, gaps 250 between the undulated ribbons 240 provide breathability to the electronic patch 200. The elastic layer 205 can usually be made of polymer materials that are breathable and allowing moisture from user's skin to permeate and released to the air. On the other hand, the more rigid first circuit layer 210 and the second circuit layer 220 are much less permeable to moisture. Large patches of rigid and dense support substrate can shield moisture from breathed out and creates discomfort to the user. The gap 250 between the undulated ribbons 240 allows the moisture or aspiration to permeate through the elastic layer 205 and significantly improve comfort to the user.

In some embodiments, an adhesive layer (not shown) can be formed under the elastic layer 205 to allow the electronic patch 200 to be adhered to user's skin. The adhesive layer can be pressure sensitive, which allows the compliant wearable patches tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

In some efforts, a ribbon of printed circuit can have a serpentine shape within the plane of the circuit board. However, in-plane serpentine shapes are not suitable for wearable electronic patches; they create twists when they are stretched, which often create cracks and can break the conductive circuits within and at the connection points with the circuit layers. Moreover, the twists also create pricks out of plane that may create discomfort to the wearing user. The presently disclosed undulated ribbons, in contrast, undulate in normal directions and can thus elongate and stretch without creating twist or excessive internal tension to the conductive circuits. The direction of the undulation being normal to flat first substrate provides significant performance and manufacturing advantages. It allows much better stretchability comparing to the undulation being parallel to flat frustrates. And it enables a simple manufacturing process by folding or pressing, etc.

In some cases, the first circuit layer 210, the second circuit layer 220 and the undulated ribbons 240 are formed on a common supporting substrate using flexible printed circuits process. There is no complex assembling required to connect the multiple circuit layers, which simplifies the manufacturing process and brings extra integrity into the products.

Figure 3A:
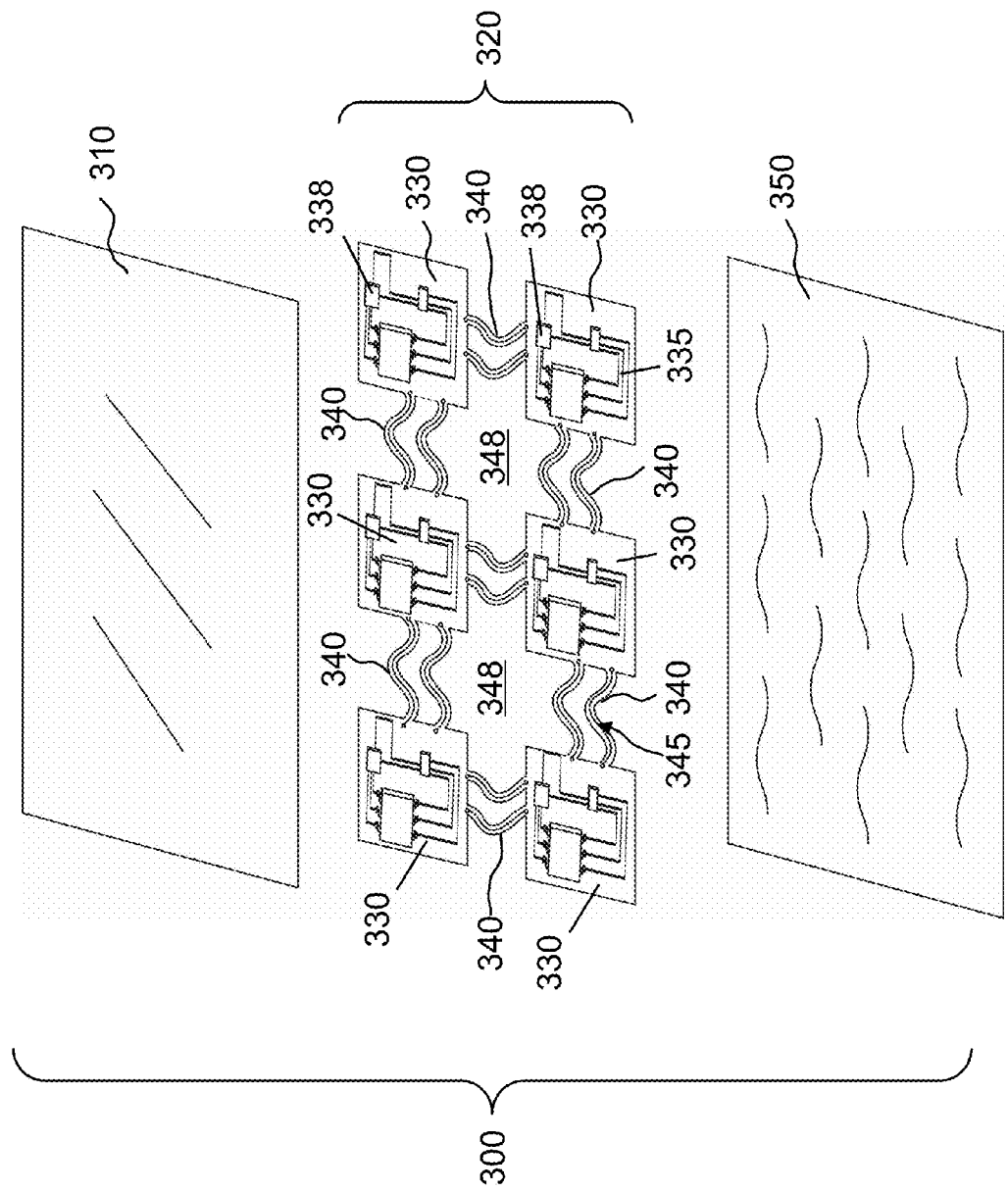
FIG. 3A is an exploded perspective view of another exemplified stretchable multi-layer electronic patch in accordance with some embodiments of the present invention.
Figure 3B:
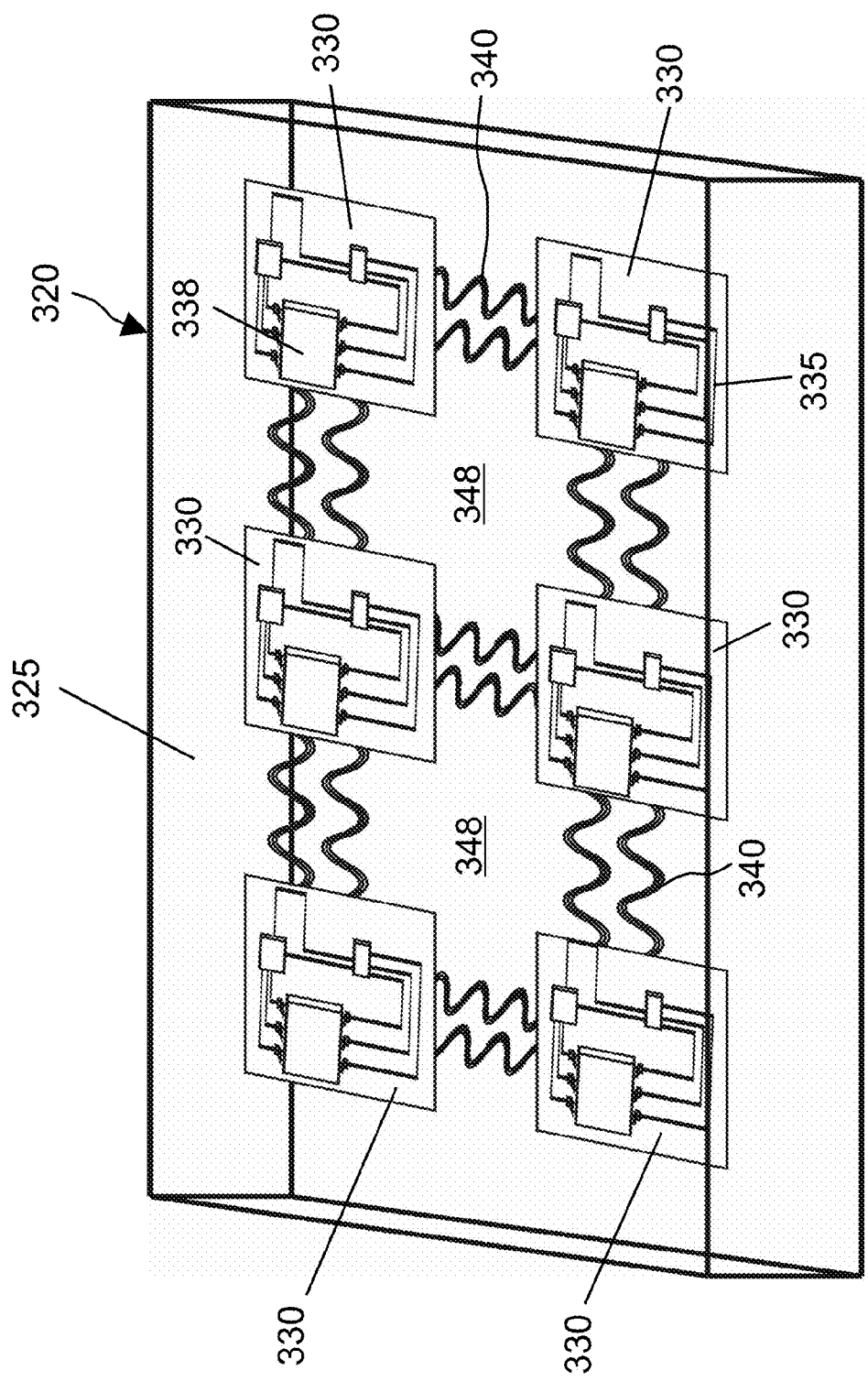
FIG. 3B is a detailed perspective view of the stretchable circuit layer in FIG. 3A.

In some embodiments, referring to FIGS. 3A and 3B, an electronic patch 300 includes an elastic layer 310, a stretchable circuit layer 320, and an adhesive layer 350 formed under the stretchable circuit layer 320. The stretchable circuit layer 320 includes an elastic layer 325 and a network of circuit modules 330 connected by undulated ribbons 340 embedded in the elastic layer 325.

The circuit modules 330 include conductive circuits 335 and semiconductor chips 338. The undulated ribbons 340 include conductive lines 345 that connect the conductive circuits 335 on the different circuit modules 330. The conductive circuits 345 can be laid on or embedded in their respective undulated ribbons 340.

The conductive circuits 335 can optionally include an antenna circuit, which by working with the semiconductor chips 338 can communicate with external devices based on NFC standard, RFID, Wi-Fi, Bluetooth, or other types of wireless communication standard. Examples of external devices include smart phones, computers, mobile payment devices, scanners and readers (e.g. RFID readers), medical devices, security systems, personal identification systems, etc. Wireless communications compatible with the electronic patch 300 includes NFC in a frequency range near 13.56 MHz, UHF RFID at about 915 MHz, Bluetooth in 2.4 GHz or 5 GHz frequency ranges, and so on.

The circuit modules 330 can include electronic components such as the semiconductor chips, resistors, capacitors, inductors, diodes (including for example photo sensitive and light emitting types), sensors, transistors, amplifiers. The sensors can also measure temperature, acceleration and movements, and chemical or biological substances. The electronic components can also include electromechanical actuators, chemical injectors, etc. The semiconductor chips 338 can perform communications, logic, signal or data processing, control, calibration, status report, diagnostics, and other functions.

The elastic layer 325 serves as a polymer matrix for the circuit modules 330, and the undulated ribbons 340. The elastic layer 310, 325 can be made of a viscoelastic polymeric material having low Young's modulus and high failure strain. In some embodiments, the elastic layer 310, 325 has Young's Modulus <0.3 Gpa. In some cases, the elastic layer 310, 325 and can have Young's Modulus <0.1 Gpa to provide enhanced flexibility and tackability. Materials suitable for the elastic layer 310, 325 include elastomers, viscoelastic polymers, such as silicone, and medical grade polyurethane that is a transparent medical dressing used to cover and protect wounds with breathability and conformation to skin.

The circuit modules 330, on the other hand, are made of sufficiently rigid materials to support to the conductive circuits 335 and the semiconductor chips 338. In some embodiments, the circuit modules 330 can be made of a material having Young's Modulus larger than 0.5 Gpa, such as in a range between 1.0-10 Gpa. Examples of materials suitable for the circuit modules 330 include Polyimide, polyester, Aramid, Composite, Glass epoxy, and Polyethylene naphalate. In some embodiments, the circuit modules 330 are thicker than 0.001 mm to allow enough strength to support the circuits and chips during manufacturing process. The circuit modules 330 can include one or more layers of conductive metals to provide additional wiring capabilities. In some embodiments, the circuit modules 330 are thinner than 0.2 mm to provide flexibility and bendability to the electronic patch 300.

The undulated ribbons 340 have curved or wavy shapes that undulate in the normal direction perpendicular to the planar directions of the electronic patch 300. The undulated ribbons 340 can also be characterized having serpentine or zigzag shapes that have turns, folds, or loops out of the plane of the electronic patch 300 or the circuit modules 330.

In FIGS. 3A and 3B, to simplifying the illustration, the undulated ribbons 340 are shown in two exemplified (i.e. X and Y) directions. In general, the undulated ribbons 340 in the disclosed electronic patches can be aligned in other orientations (ranging from 0 to 360 degrees relative an edge of a circuit module 330) within the plane the circuit modules 330.

When the electronic patch 300 is worn on a user's skin, the user skin often stretches (or compresses) in response to user's body (thus muscle) movements, thus conforming to user's skin in different moving positions. In response, the undulated ribbons 340 can elongate by unfolding at least partially some of their curved or wavy shapes without exerting excessive tensions on the conductive circuits 335, or on the semiconductor chips 338. Thus the conductive circuits 335 and electronic components can stay intact and maintain normal functions under repeated stretches and compressions when the electronic patch 300 is worn on a user's skin. It should be noted that the undulated ribbons 340 can be laid out in orthogonal or other directions within the plane of the stretchable circuit layer 320. The electronic patch 300 is stretchable and compressible in any in plane direction.

Moreover, gaps 348 between the undulated ribbons 340 provide breathability to the electronic patch 300. The elastic layers 325 and 310 can usually be made of polymer materials that are breathable and allowing moisture from user's skin to permeate and released to the air. On the other hand, the more rigid circuit modules 330 are much less permeable to moisture. Large patches of rigid and dense support substrate can shield moisture from breathed out and creates discomfort to the user. The gap 348 between the undulated ribbons 340 allows the moisture or aspiration to permeate through the elastic layers 325 and 310, and to significantly improve comfort to the user.

In some cases, the circuit modules 330 and the undulated ribbons 340 can be formed on a common piece supporting substrate using flexible printed circuits process. There is no complex assembling required to connect the multiple circuit layers, which simplifies the manufacturing process and brings extra integrity into the products.

The adhesive layer 350 allows the electronic patch 300 to be adhered to user's skin. The adhesive layer can be pressure sensitive, which allows the compliant wearable patches tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

Referring to FIGS. 4A-4B, the disclosed stretchable wearable electronic patches can be fabricated using one or more of the following steps. A single flat circuit layer 400 is first prepared. The flat circuit layer 400 includes semiconductor chips 218, 228 and conductive circuits 215, 225 (not shown), the conductive circuit 245, and other electronic components that are on the first circuit layer 210, the second circuit layer 220, and the undulated ribbons 240 shown in FIGS. 2A and 2B.

As shown in FIG. 4A, the flat circuit layer 400 is sandwiched between an upper mold 410 and a lower mold 430. The upper mold 410 and the lower mold 430 respectively include recesses 415, 425 and 435, 445 for keeping space for semiconductor chips 218, 228 during pressing. The recesses 415, 435 are paired up to provide clearance for the semiconductor chip 218. The recesses 425, 445 are paired up to provide clearance for the semiconductor chip 228. The upper mold 410 and the lower mold 430 respectively include recesses 420, 440 which have undulated contours compatible with the shapes of the undulated ribbons 240. When the upper mold 410 and the lower mold 430 are held pressed against each other under pressure, a (middle) portion of the flat circuit layer 400 is pressed following the contours of the recesses 420, 440, which form the undulated ribbons 240 with undulation in the layer normal direction.

After pressing, referring to FIG. 4B, the flat circuit layer 400 is transformed into the first circuit layer 210 and the second circuit layer 220 that include substantially flat substrates 211, 221, the undulated ribbons 240 that connects the first circuit layer 210 and the second circuit layer 220. The undulated ribbons 240 is embedded with or laid on with the conductive circuit 245. The shapes of the recesses 420 and 440 are configured to produce curved or wavy shapes in the undulated ribbon 240 that undulate in the normal direction perpendicular to the planar directions of the flat circuit layer 400. The undulated ribbon 240 can also be characterized having serpentine or zigzag shapes that have turns, folds, or loops out of the plane or the first circuit layer 210 and the second circuit layer 220.

Afterwards, referring to FIG. 4C, the elastic layer 205 is formed around the first circuit layer 210, the second circuit layer 220, and the undulated ribbons 240, which produces the electronic patch 200. The elastic layer 205 can be formed by lamination or molding, including but not limited to, injection molding, transfer molding, vacuum molding, matrix molding, rotational molding, extrusion molding, blow molding, etc., by appropriate polymeric materials as described above. The elastic layer 205 serves as a polymer matrix for the first circuit layer 210, the second circuit layer 220, and the undulated ribbons 240, which protects the electronic components and circuit and provides further flexibility and comfort.

In some embodiments, referring to FIG. 5A, a foldable circuit layer 500 includes a foldable support substrate 505 and electronic elements 510. The electronic elements 510 can include portions of conductive circuits, semiconductor chips, resistors, capacitors, inductors, diodes (including for example photo sensitive and light emitting types), sensors, transistors, and amplifiers. The sensors can also measure temperature, acceleration and movements, and chemical or biological substances. The electronic components can also include electromechanical actuators, chemical injectors, etc. The semiconductor chips can perform communications, logic, signal or data processing, control, calibration, status report, diagnostics, and other functions. The foldable support substrate 505 can also include one or more layers of conductive metals to provide additional wiring capabilities.

The foldable support substrate 505 is made of sufficiently rigid materials to support to the electronic elements 510. In some embodiments, the foldable support substrate 505 can have Young's Modulus larger than 0.5 Gpa, such as in a range between 1.0-10 Gpa. Examples of materials suitable for the foldable support substrate 505 include Polyimide, Polyethylene, terephthalate, PEEK, Polyester, Aramid, Composite, Glass epoxy, and Polyethylene naphalate.

In the foldable circuit layer 500, the electronic elements 510 are distributed in different portions or sections separated by fold lines 515. The fold lines 515 can be prepared by molding, pressing, and scoring. The foldable circuit layer 500 also includes flexible conductive lines laid out across the fold lines 515, which connect different portions of the electronic elements 510. In some embodiments, the fold lines 515 are substantially parallel to each other.

Referring to FIG. 5B, the foldable circuit layer 500 can be pressed, creased, or folded to prepare an undulated circuit layer 520. After folding, the cross-section of the foldable circuit layer 500 has a zigzag shape that undulates out of the plane of the originally foldable circuit layer 500.

Figure 5C:
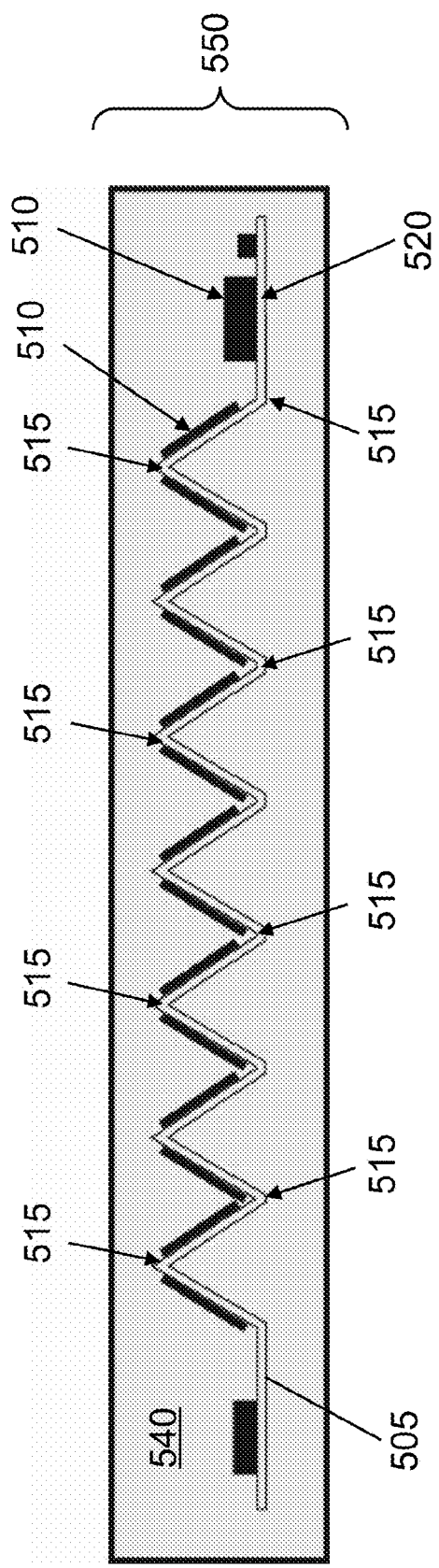

In some embodiments, referring to FIG. 5C, an elastic layer 540 can be formed around the undulated circuit layer 520 similar to what is shown in FIG. 4C to produce an electronic patch 550. The elastic layer 540 can be formed by laminated or molded, including but not limited to, injection molding, transfer molding, vacuum molding, matrix molding, rotational molding, extrusion molding, blow molding, etc. by appropriate polymeric materials as described above. The elastic layer serves as a polymer matrix for the undulated circuit layer 520, which protects the electronic components and circuit and provides further flexibility and comfort.

One difference between the electronic patch 550 and the electronic patch 200 shown in FIGS. 2A-2B, 4A-4C is that all or most electronic components and conductive circuits in the electronic patch 550 are on undulated portions of the foldable support substrate 505 while in the electronic patch 200 most electronic components are positioned on flat circuit layers connected by one or more undulated circuit layers.

Figure 6A:
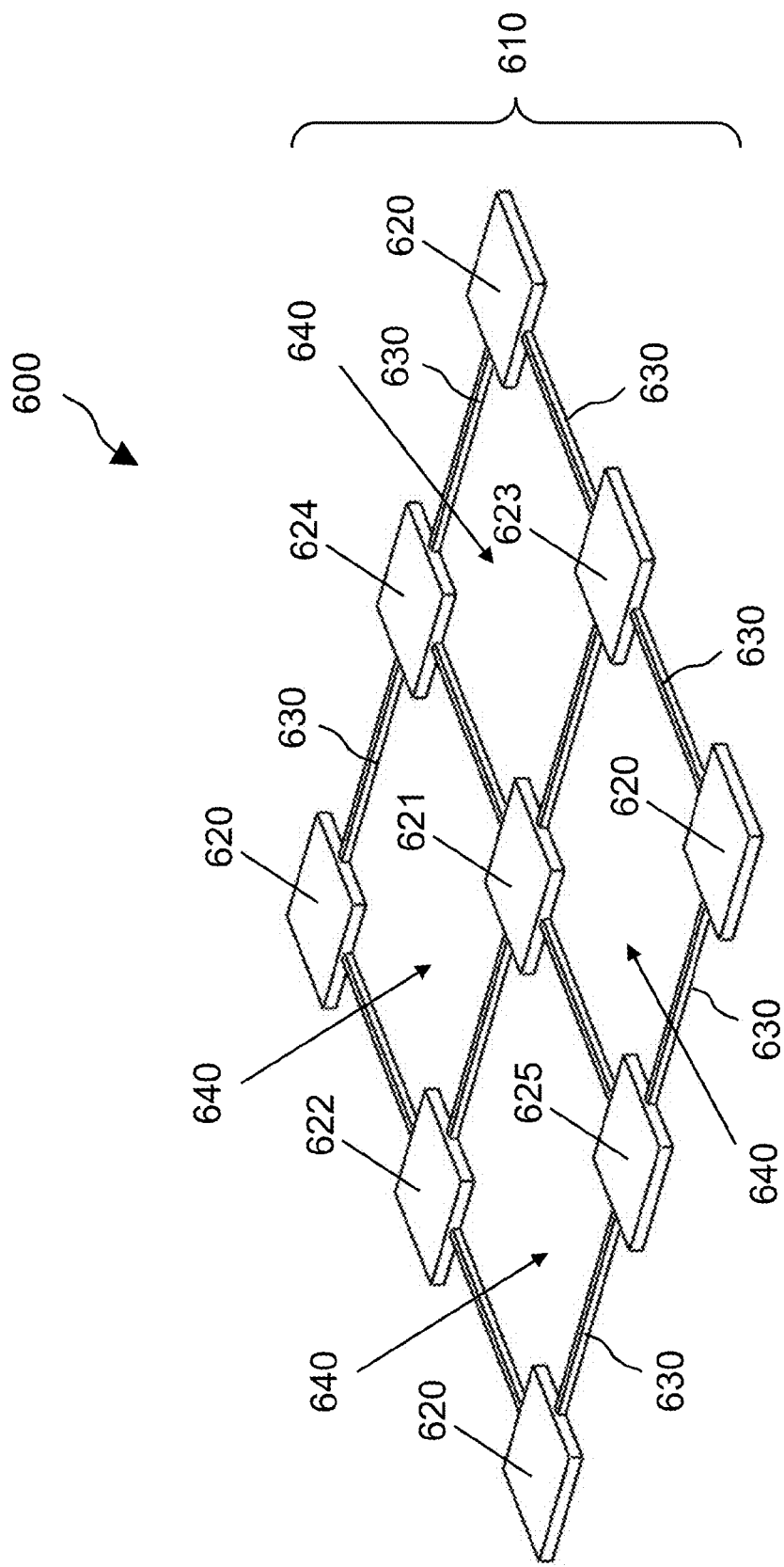
FIGS. 6A-6D are perspective views of another exemplified stretchable wearable electronic patch having foldable circuit layer in accordance with some embodiments of the present invention.

In some embodiments, referring to FIG. 6A, a foldable circuit layer 600, which is compatible with the presently disclosed stretchable electronic patch, includes a foldable network 610 of electronic modules 620-625 connected by flexible straps 630. The electronic modules 620-625 can include electronic components such as conductive circuits, semiconductor chips, resistors, capacitors, inductors, diodes (including for example photo sensitive and light emitting types), sensors, transistors, and amplifiers. The sensors can also measure temperature, acceleration and movements, and chemical or biological substances. The electronic components can also include electromechanical actuators, chemical injectors, etc. The semiconductor chips can perform communications, logic, signal or data processing, control, calibration, status report, diagnostics, and other functions. The electronic components in the plurality of electronic modules can include an antenna circuit that can receive or transmit wireless signals in communications with the external device.

The flexible straps 630 is formed a bendable or elastic material and includes conductive circuits that connect the conductive circuits, semiconductor chips, and other electronic components in different electronic modules 620-625. The electronic modules 620-625 and the flexible straps 630 define holes 640 in between, which form the foldable network 610 in the foldable flat circuit layer 600. In some embodiments, the flexible straps 630 and the substrate in the electronic modules 620-625 can be formed from a same layer of substrate by techniques such as cutting, laser ablation, punching etc.

Figure 7:
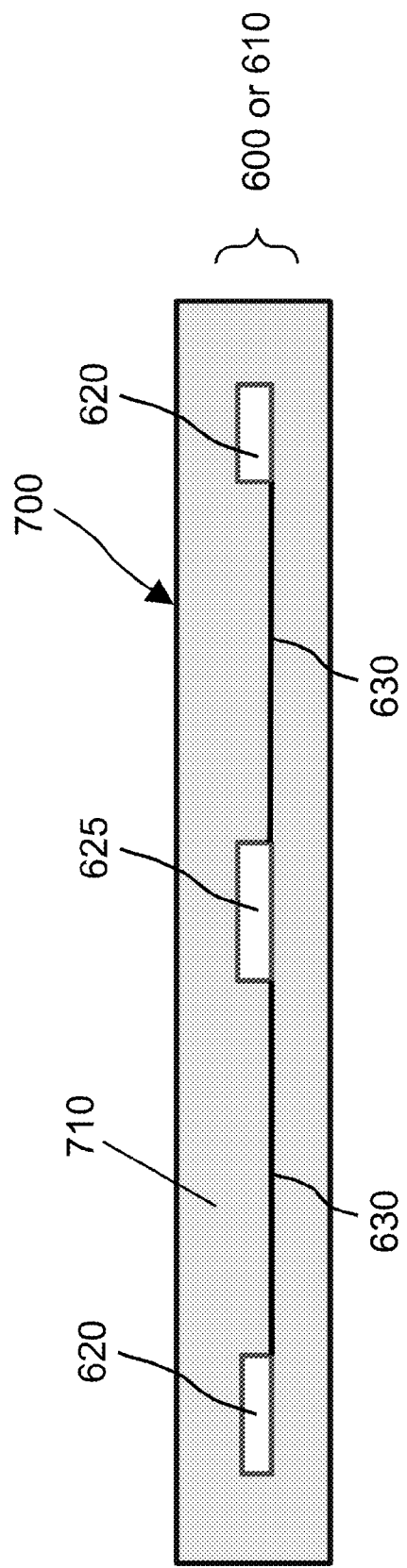
FIG. 7 is a cross-sectional view of a stretchable wearable electronic patch comprising the exemplified stretchable wearable electronic patch having foldable circuit layer in FIGS. 6A-6D.

Referring to FIG. 7, an electronic patch 700 can further include an elastic layer 710 in which the foldable flat circuit layer 600 or the foldable network 610 is embedded. The elastic layer 710, similar to above described elastic layers (205 in FIG. 2A and 325 in FIG. 3B), serves as an elastic (polymer) matrix for the electronic modules 620-625 and the flexible straps 630. The elastic layer 710 can be made of a viscoelastic polymeric material having low Young's modulus and high failure strain. In some embodiments, the elastic layer 710 can have Young's Modulus <0.3 Gpa. In some cases, the elastic layer and can have Young's Modulus <0.1 Gpa to provide enhanced flexibility and tackability. Materials suitable for the elastic layer include elastomers, viscoelastic polymers, such as silicone, and medical grade polyurethane that is a transparent medical dressing used to cover and protect wounds with breathability and conformation to skin. The elastic layer 710 are sufficiently flexible to permit and conform to the folding or crumpling of the foldable flat circuit layer 600 or the foldable network 610.

The electronic modules 620-625, on the other hand, are formed on substantially flat support substrates made of sufficiently rigid materials to support to the semiconductor chips and other electronic components. In some embodiments, the electronic modules 620-625 can be made of a material having Young's Modulus larger than 0.5 Gpa, such as in a range between 1.0-10 Gpa. Examples of materials suitable for the circuit modules 330 include Polyimide, polyester, Aramid, Composite, Glass epoxy, and Polyethylene naphalate. In some embodiments, electronic modules 620-625 are thicker than 0.001 mm to allow enough strength to support the circuits and chips during manufacturing process. The electronic modules 620-625 can include one or more layers of conductive metals to provide additional wiring capabilities.

Figure 6B:
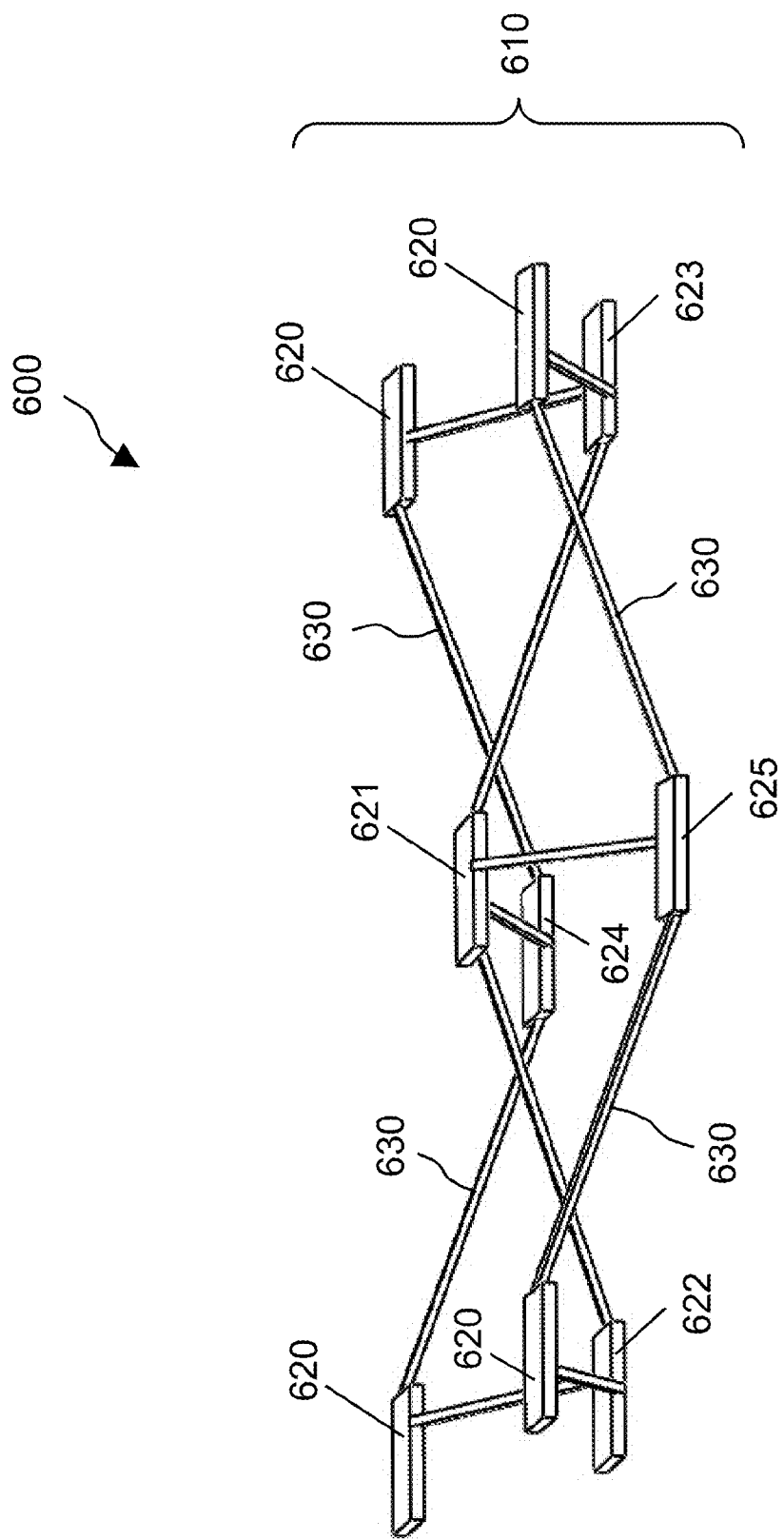
Figure 6C:
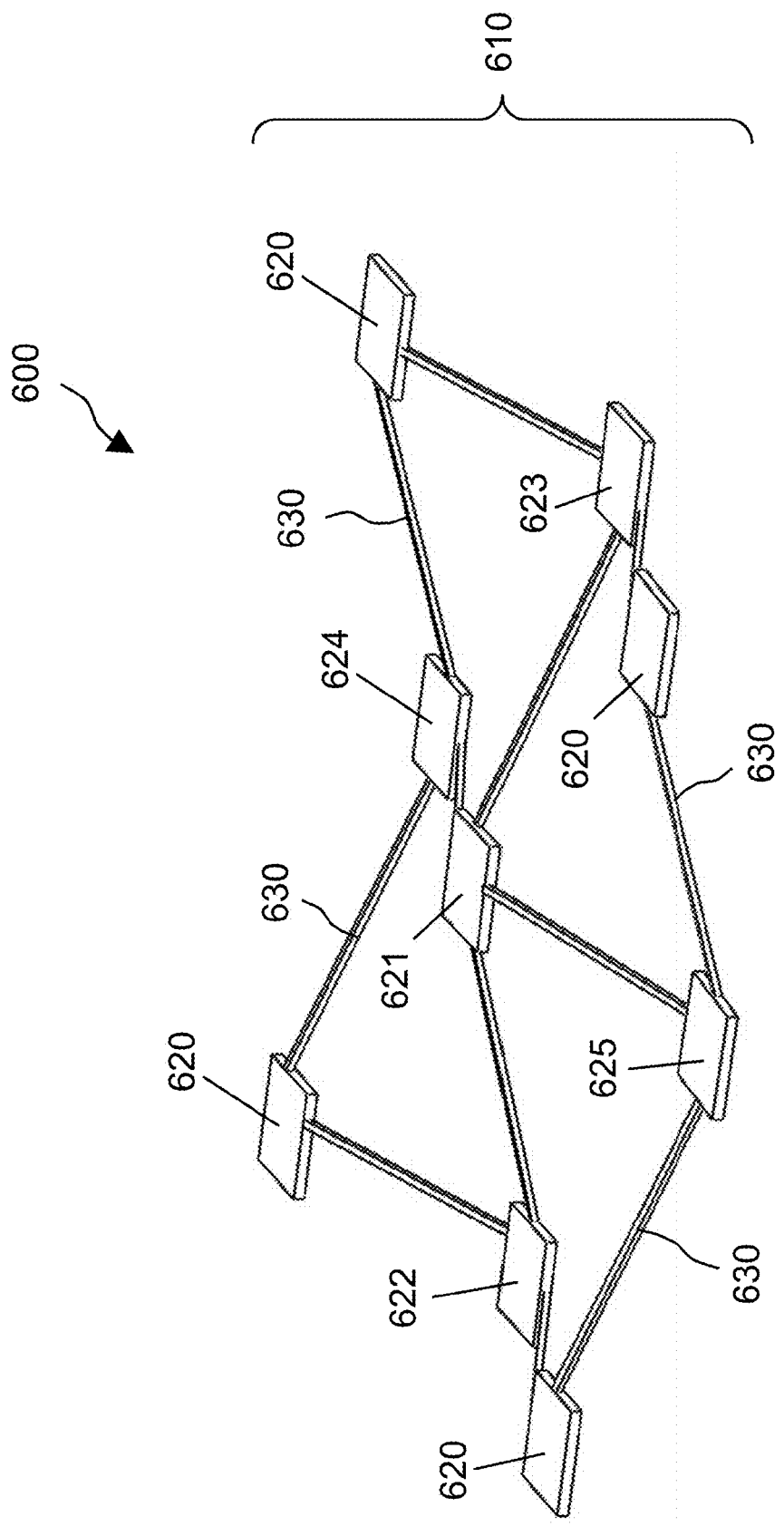
Figure 6D:
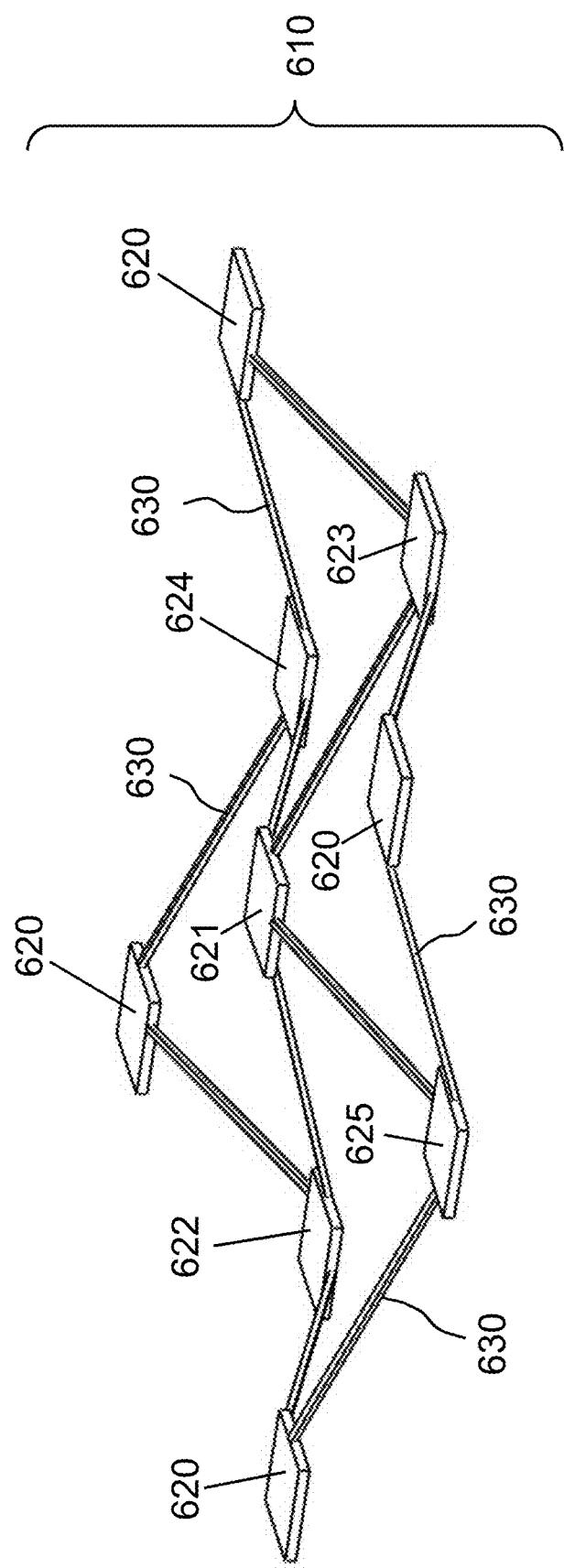

FIG. 6A shows the foldable network 610 in a flat configuration. Referring to FIGS. 6B-6D, the foldable network 610 can be folded or crumpled in different configurations. In should be noted that the foldable circuit layer 600 can not only fold along straight lines in the planar directions, similar to the foldable circuit layer 500 in FIG. 5A, the foldable circuit layer 600 can also simultaneously fold in two directions as shown in FIGS. 6B-6D. In other words, unlike the electronic elements 510 that are folded in parallel fold lines 515 (FIGS. 5A-5C), neighboring electronic modules 620-625 within same row or column can undulate in opposite directions the layer normal direction. For example, the electronic module 621 is aligned with two neighboring electronic modules 622, 623 in a same row and lined up with other neighboring electronic modules 624,625 in a same column. The electronic module 621 can be displaced in the layer normal direction opposite to the undulation directions of the electronic modules 622-625.

In another view, the foldable network 610 and the foldable circuit layer 600 can crumple, fold, or wrinkle locally instead of folding along parallel fold lines in predetermine directions. In some embodiments, the foldable network 610 and the foldable circuit layer 600 can also form origami-type structures.

An advantage of the above disclosed foldable circuit layers is that they can be very flexible in adapting to changes in body shape and positions of the person who wears the electronic patch. The their foiled or crumpled states, the foldable circuit layers can characterized by thickness that are scaled in mathematically fractal relationships relation to the average distance between the neighboring electronic modules, which provides flexibility and stretchability along both the normal and planar directions.

It should be noted that other types of foldable networks or foldable circuit layers are also compatible with the presently disclosed electronic patches. For example, the flexible straps can be configured in helical or coiled shapes to provide further flexibility. Moreover, the foldable networks in the foldable circuit layers can be implemented in a knitted or weaved structures to support stretchability, flexibility, as well as reliable mechanical strength and durability.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the applications and the types of electronic components of the disclosed electronic patches are not limited by the examples given above; they can be applicable to many other fields. The materials suitable for the different layers of the electronic patches are also not limited by the examples provided. The layouts and forms of the elastic layer, the undulated and the flat circuit layer, the breathing openings, and the electronic components can have other configurations without deviating from the present invention.

What is claimed is:

1. An electronic patch, comprising:
a foldable circuit layer that defines a layer normal direction perpendicular to the foldable circuit layer, comprising:
a foldable network, comprising:
a plurality of electronic modules comprising a plurality of electronic components, wherein the plurality of electronic modules include a first electronic module and second electronic modules on two sides of the first electronic module; and
flexible straps that connect the plurality of electronic modules, wherein the flexible straps comprise conductive circuit that are conductively connected with the plurality of electronic components in the plurality of electronic modules,
wherein the first electronic module is displaced along the layer normal direction perpendicular to the foldable circuit layer, wherein the second electronic modules are displaced opposite to the layer normal direction; and
an elastic layer that encloses the foldable circuit layer.

2. The electronic patch of claim 1, wherein the second electronic modules are positioned on two sides of the first electronic module along a first planar direction defined by the foldable circuit layer, wherein the plurality of electronic modules comprises:
 third electronic modules on two sides of the first electronic module along a second planar direction,
 wherein the third electronic modules are displaced opposite to the layer normal direction.

3. The electronic patch of claim 2, wherein the first electronic module and the second electronic modules are positioned in a row, wherein the first electronic module and the third electronic modules are positioned in a column perpendicular to the row.

4. The electronic patch of claim 1, wherein the plurality of electronic modules and the flexible straps define holes therein and form the foldable network comprising multiple holes, which in part forms the foldable network.

5. The electronic patch of claim 1, wherein the elastic layer has a Young's Modulus lower than 0.3 Gpa.

6. The electronic patch of claim 1, wherein the elastic layer comprises an elastomeric material or a viscoelastic polymeric material.

7. The electronic patch of claim 1, wherein the plurality of electronic modules are formed on support substrates.

8. The electronic patch of claim 7, wherein the support substrate has a Young's Modulus higher than 0.5 Gpa.

9. The electronic patch of claim 7, wherein the first support substrate comprises Polyimide, Polyethylene, Terephthalate, PEEK, Polyester, Aramid, Composite, Glass epoxy, and Polyethylene naphalate.

10. The electronic patch of claim 1, wherein the electronic components in the plurality of electronic modules comprise one or more semiconductor chips.

11. The electronic patch of claim 10, wherein the one or more semiconductor chips are configured to wirelessly communicate with an external device.

12. The electronic patch of claim 11, wherein the electronic components in the plurality of electronic modules comprise an antenna circuit configured to receive or transmit wireless signals in communications with the external device.

13. The electronic patch of claim 12, wherein the one or more semiconductor chips in combination with the first conductive circuit or the second conductive circuit are configured to wirelessly communicate with the external device based on near field communication (NFC), Wi-Fi, Bluetooth, or RFID wireless communication standard.

14. The electronic patch of claim 1, wherein the electronic components in the plurality of electronic modules comprise capacitors, inductors, resistors, metal pads, diodes, transistors, or amplifiers.

15. An electronic patch, comprising:
 a foldable circuit layer that defines a layer normal direction perpendicular to the foldable circuit layer, comprising:
  a foldable substrate comprising a plurality of sections separated by fold lines parallel to the substrate, wherein the foldable substrate is configured to be folded along the fold lines, wherein the plurality of sections are tilted relative to the layer normal direction;
  a conductive circuit; and
  a plurality of electronic components on different sections in the plurality of sections, wherein the conductive circuit is configured to connect the plurality of electronic components across the plurality of sections, wherein the substrate is folded along the fold lines that are parallel to the substrate; and
 an elastic layer that encloses the foldable circuit layer.

16. The electronic patch of claim 15, wherein cross-sectionally the substrate has a zigzag shape, wherein neighboring sections in the plurality of sections are alternately tilted to the layer normal direction.

17. The electronic patch of claim 15, wherein the fold lines are substantially parallel to each other.

\* \* \* \* \*